United States Patent [19]

Sofranko

[11] Patent Number: 4,879,427
[45] Date of Patent: Nov. 7, 1989

[54] METHANE CONVERSION

[75] Inventor: John A. Sofranko, West Chester, Pa.

[73] Assignee: Atlantic Richfield Company, Los Angeles, Calif.

[21] Appl. No.: 291,701

[22] Filed: Dec. 29, 1988

[51] Int. Cl.⁴ .............................................. C07C 2/00
[52] U.S. Cl. .................................... 585/500; 585/415; 585/417; 585/636; 585/654; 585/541; 585/921; 585/926; 585/943; 585/700
[58] Field of Search ............... 585/943, 636, 500, 921, 585/926, 415, 417, 541, 654, 700

[56] References Cited

U.S. PATENT DOCUMENTS

| | | | |
|---|---|---|---|
| 4,513,164 | 4/1985 | Olah | 585/700 |
| 4,634,800 | 1/1987 | Withers, Jr. et al. | 585/500 |
| 4,670,619 | 6/1987 | Withers, Jr. et al. | 585/500 |
| 4,727,205 | 2/1988 | Veleny et al. | 585/407 |
| 4,731,498 | 3/1988 | Devries et al. | 585/415 |

*Primary Examiner*—Asok Pal
*Attorney, Agent, or Firm*—William C. Long

[57] ABSTRACT

A process is provided for the oxidative conversion of methane to higher hydrocarbons wherein a mixture of methane and gaseous oxidant is contacted at reaction conditions with a solid oxidative contact agent which is essentially free of reducible metal oxide, the oxidative conversion taking place in the presence of a chalcogen promoter.

8 Claims, 1 Drawing Sheet

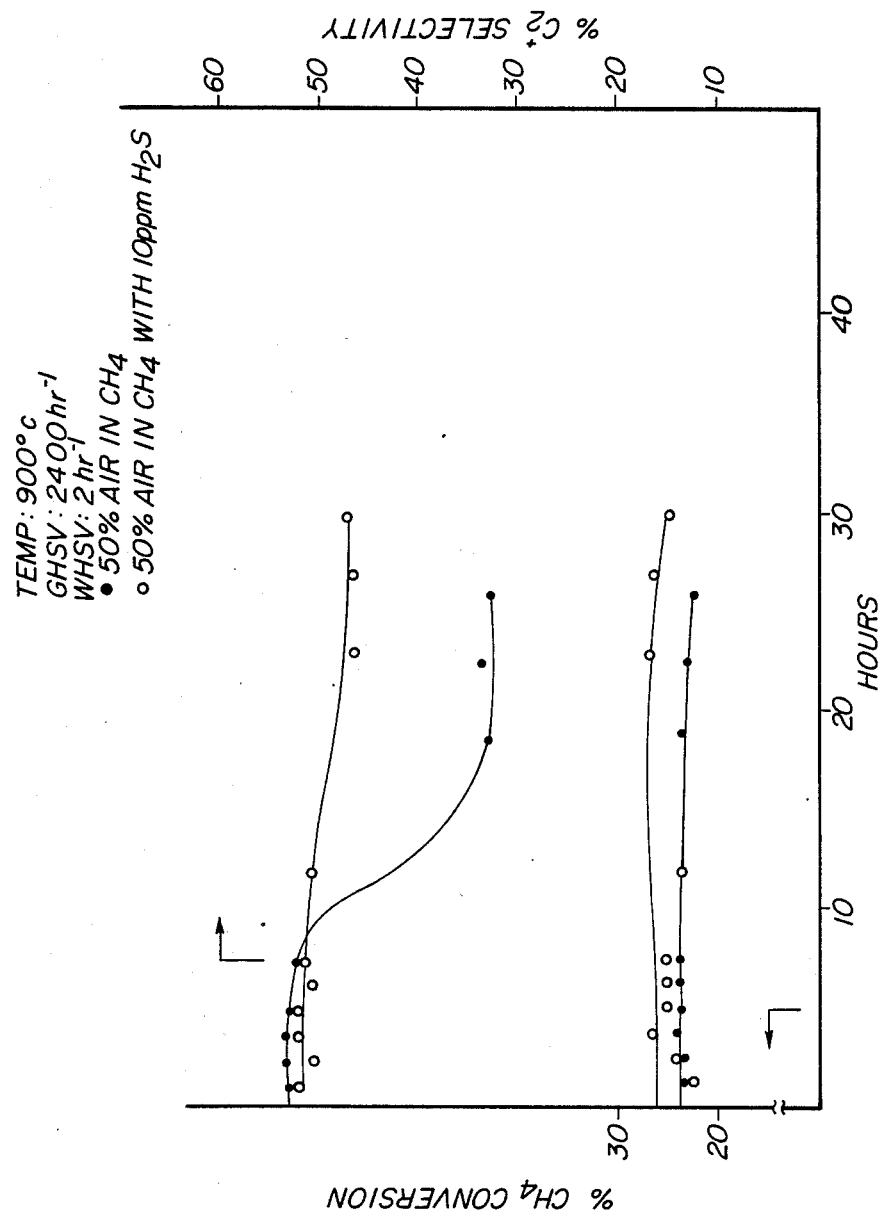
FIG-1 METHANE/AIR COFEED LIFE TEST ON 1% Li ON MgO

METHANE CONVERSION

BACKGROUND OF THE INVENTION

1. Field of the Invention

The present invention relates to the conversion of methane to higher hydrocarbons. In particular, the invention relates to oxidative conversion of methane to higher hydrocarbons by contacting a mixture of methane and a gaseous oxidant with a catalyst contact solid which does not contain a reducible metal oxide, the improvement being that the conversion is carried out in the presence of a chalcogen promoter.

2. Description of the Prior Art

Methane is found in large quantities in gaseous form in somewhat remote regions of the world. The transportation of this methane to areas where it can be utilized is relatively inefficient.

Considerable work has been carried out relating to the conversion of methane to higher molecular weight hydrocarbons which are readily condensable and which can be conveniently transported in liquid form. In this regard, reference is made to the following U.S. patents which are concerned with conversion of methane to higher hydrocarbons: U.S. Pat. Nos. 4,443,649; 4,444,984; 4,443,648; 4,443,645; 4,443,647; 4,443,644; 4,443,646; 4,499,323; 4,499,324; 4,593,139; 4,489,215; 4,499,322; 4,495,374; 4,544,784; 4,544,785; 4,547,610; 4,547,611; 4,517,398; 4,544,787; 4,547,608; 4,544,786; 4,568,785; 4,523,049; 4,523,050 and the like.

The oxidative conversion of methane to higher hydrocarbons can be carried out using solid contact agents which contain reducible metal oxides in both the redox mode, wherein the contact agent is alternately contacted with methane and oxidizing gas, and in the cofeed mode wherein the contact agent is contacted with a mixture of methane and gaseous oxidant. Redox mode operation is illustrated, for example, in U.S. Pat. Nos. 4,443,649; 4,444,984; 4,443,648; 4,443,645; 4,443,647; 4,443,644; and 4,443,646. Cofeed mode operation is illustrated, for example, in U.S. Pat. No. 4,523,049; 4,523,050 and 4,634,800.

In systems wherein reducible metal oxides are employed as an essential component of the contact solid, the use of chalcogen additives has been taught for operation in both redox and cofeed mode; see U.S. Pat. No. 4,544,785 and 4,670,619 respectively.

The oxidative conversion of methane to higher hydrocarbons can also be carried out in the cofeed mode using solid catalyst contact agents which are of a non-acidic nature and which do not contain reducible metal oxide as an active component. See, for example, copending applications Ser. Nos. 738,110 and 738,114, each filed May 24, 1985 the contents of which are incorporated herein by reference and made part hereof. See also published European Patent Applications Nos. 0196541 and 0198251 which are based on U.S. applications Ser. Nos. 713,653 and 713,652 respectively, each filed Mar. 19, 1985. In these later references there is provided the teaching that it is desirable to remove hydrogen sulfide from methane-containing feed gas prior to oxidative conversion.

Despite significant advances in the art of oxidative conversion of methane to higher hydrocarbons, a disadvantage has been the general decline in activity and selectivity achieved with various contact agents over time.

SUMMARY OF THE INVENTION

In accordance with the present invention, there is provided an improved process for oxidative conversion of methane to higher hydrocarbons wherein a mixture of methane and gaseous oxidant is contacted at reactive conditions with a solid catalyst contact agent which does not contain reducible metal oxide, the improvement being that the oxidative conversion is carried out in the presence of a chalcogen promoter. Through practice of the invention, significant process improvements are achieved especially with regard to production of higher hydrocarbons over extended reaction times.

BRIEF DESCRIPTION OF DRAWING

The attached drawing presents a graphical comparison illustrating the improved results achieved by the invention.

DESCRIPTION OF THE INVENTION

In addition to methane, the hydrocarbon feedstock employed in the method of this invention may contain other hydrocarbon or non-hydrocarbon components. The methane content of the feedstock, however, will typically be within the range of about 40 to 100 vol.%, preferably within the range of about 80 to 100 vol.%, more preferably within the range of about 90 to 100 vol.%.

The gasous oxidant is selected from the group consisting of molecular oxygen, oxides of nitrogen, and mixtures thereof. Preferably, the gaseous oxidant is an oxygen-containing gas. Air is preferred oxygen-containing gas. Suitable oxides of nitrogen include $N_2O$, $NO$, $N_2O_3$, $N_2O_5$, and $NO_2$. Nitrous oxide ($N_2O$) is a presently preferred oxide of nitrogen.

The ratio of hydrocarbon feedstock to gaseous oxidant gas is not narrowly critical to the present invention. However, the ratio will desirably be controlled to avoid the formation of gaseous mixtures within the flammable region. The volume ratio of hydrocarbon/gaseous oxidant is preferably within the range of about 0.1–100:1, more preferably within the range of about 1–50:1. Methane gaseous oxidant feed mixtures containing about 50 to 90 volume % methane have been found to comprise a desirable feedstream. Chalogen promoters are introduced with the gaseous feedstreams flowing to the process. Suitable promoters include free chalogen gas or a chalogen compound. Suitable chalogen compounds include hydrogen chalogenides, chalcogen oxides, ammonium chalogenides, aliphatic chalogenides (e.g., methyl sulfide, methylene sulfide, ethyl sulfide, amyl sulfide and allyl sulfide) cycloaliphatic chalcogenides (e.g., cyclohexyl sulfide), chalcogen substituted aliphatic acides, amine chalcogenide, salts, and the like. Presently preferred chalcogen promoters are sulfur and compounds thereof, especially methyl sulfide, hydrogen sulfide and sulfur dioxide.

The amount of promoter introduced is preferably such that the promoter content of the combined gaseous feedstrems (e.g., stabilizer, gas comprising methane, and gaseous oxidant) is less than about 1 vol.%, more preferably within the range of about 1 ppm to 1 vol.%, still more preferably within the range of about 2 to 1000 ppm. Optimum quantities are dependent on the stabilizer selected, the particular contact solid employed and on the process temperature.

In accordance with the invention known solid non-acidic oxidative contact agents are employed which are essentially free from reducible metal oxides. Such contact agents are described in said copending application 738,110 filed May 24, 1985, for example.

Especially preferred contact agents are the alkaline earth oxides, especially MgO and CaO. Other suitable metal oxides are $SiO_2$, alpha-$Al_2O_3$, $La_2O_3$, $ThO_2$, $TiO_2$, and $ZrO_2$. Such materials are relatively stable under the conditions of the present process.

An especially preferred solid contact agent employed in the present process comprises an alkali metal component associated with the nonacidic solids described above. Alkali metals are selected from the group consisting of Li, Na, K, Rb and Cs. Preferred components are Li, Na and compounds thereof. The wt. % loading of the alkali metal component (expressed as wt.% alkali metal in composite) is preferably within the range of about 0.01 to 99 wt.%, more preferably within the range of about 0.1 to 10 wt.%.

Phosphorus components may also be added to the solid. Again, the amount contained in the solid is not narrowly critical.

Composite solids can be prepared by any suitable method. For example, alkali-promoted solids may be prepared with such methods as adsorption, impregnation, precipitation, coprecipitation and dry mixing. When phosphorus is incorporated into the catalyst, it is desirably provided in the form of a phosphate of an alkali metal.

A suitable method of preparation is to impregnate a support with solutions of the desired metals. Suitable compounds useful for impregnation include the acetates, acetylacetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solid is calcined, preferably in air, at a temperature within the range of about 300° to 1200° C. Particular calcination temperatures will vary depending upon the particular metal compound or compounds employed.

Halogen promoeters can be used as described in said 738,110 and 738,114 applications. Halogens are selected from the group consisting of F, Cl, Br and I. Preferred promoters are Cl, Br, and compounds thereof. Chlorine-containing promoters are particularly preferred.

Halogen promoters are preferably introduced into the process with gaseous feedstreams flowing to the process.

Stream addition can advantageously be employed as set forth in copending application Ser. No. 07/014,405 filed Feb. 13, 1987, the disclosure of which is incorporated herein by reference.

Operating temeratures are generally selected within the range of about 300° to 1200° C., more preferably within the range of about 500° to 1000° C.

Operating pressures for the methane contacting step are not critical to the presently claimed invention. However, both general system pressure and partial pressures of methane and oxygen have been found to effect overall results. Preferred operating pressures are within the range of about 0.1 to 30 atmospheres.

The space velocity of the gaseous reaction streams are similarly not critical to the presently claimed invention, but have been found to effect overall results. Preferred total gas hourly space velocities are within the range of about 10 to 100,000 $hr^{-1}$, more preferably within the range of about 600 to 40,000 $hr^{-1}$.

The contact solids may be maintained in the zone as fixed, moving, or fluidized beds of solids. A fixed bed of solids is currently preferred for the method of this invention.

The effluent from the contact zone contains higher hydrocarbon products (e.g., ethylene, ethane and other light hydrocarbons), carbon oxides, water uncreased hydrocarbon (e.g., methane) and oxygen, and other gases present in the oxygen-containing gas fed to the contact zone. Higher hydrocarbons may be recovered from the effluent and, if desired, subjected to further processing using techniques known to those skilled in the art. Unreacted methane may be recovered and recycled to the contact zone.

The invention is further illustrated by reference to the following example. Experimental results reported below include conversion and selectivities calculated on a carbon mole basis.

Comparative methane conversion runs were conducted over Li on MgO catalysts. The catalysts were prepared by slurrying $Li_2CO_3$ and MgO in water, drying the slurry, and calcining the dried product 16 hours at 900° C. in air. Amounts were used calculating to form a catalyst containing 1 wt.% Li (as the element) on MgO.

In the run according to this invention methane containing 10 ppm $H_2S$ was fed at 100 cc/min together with 100 cc/min air to the reaction. In the comparative run methane was fed at 100 cc/min together with 100 cc/min air.

Table 1 shows results in accordance with the invention, Table 2 shows results of the comparative run.

TABLE 1

| Hrs. | % $CH_4$ Conv. | % Selectivity | | | | | | | |
|---|---|---|---|---|---|---|---|---|---|
| | | $C_2=$ | $C_2$ | $C_3$ | $\geq C_4$ | CO | Coke | $CO_2$ | $C_2+$ |
| 1 | 22.1 | 37.1 | 8.5 | 3.5 | 3.2 | 34.9 | 0 | 12.8 | 52.3 |
| 2 | 23.6 | 35.4 | 8.4 | 3.2 | 3.2 | 36.1 | 0 | 13.7 | 50.2 |
| 3 | 26.4 | 37.0 | 8.3 | 3.7 | 3.2 | 34.4 | 0 | 13.3 | 52.2 |
| 4 | 24.7 | 36.4 | 10.0 | 3.0 | 2.7 | 33.7 | 0 | 14.1 | 52.1 |
| 5 | 25.4 | 35.6 | 9.4 | 3.0 | 2.5 | 35.3 | 0 | 14.2 | 50.5 |
| 6 | 24.9 | 36.0 | 9.9 | 3.0 | 2.5 | 34.9 | 0 | 13.7 | 51.4 |
| 12 | 23.4 | 35.6 | 10.0 | 3.0 | 2.3 | 35.9 | 0 | 13.3 | 50.8 |
| 23 | 27.0 | 33.2 | 8.4 | 2.8 | 2.1 | 39.0 | 0 | 14.5 | 46.5 |
| 27 | 26.5 | 33.3 | 8.3 | 2.9 | 2.0 | 38.9 | 0 | 14.6 | 46.5 |
| 30 | 24.6 | 33.6 | 8.5 | 2.7 | 2.2 | 39.3 | 0 | 13.7 | 47.0 |

TABLE 2

| Hrs. | % $CH_4$ Conv. | % Selectivity | | | | | | | |
|---|---|---|---|---|---|---|---|---|---|
| | | $C_2=$ | $C_2$ | $C_3$ | $\geq C_4$ | CO | Coke | $CO_2$ | $C_2+$ |
| 1 | 23.1 | 38.6 | 5.6 | 3.7 | 4.9 | 33.7 | 0 | 13.4 | 52.9 |
| 2 | 23.3 | 39.6 | 6.6 | 3.8 | 2.7 | 32.9 | 0 | 14.4 | 52.7 |
| 3 | 23.9 | 39.8 | 7.1 | 3.9 | 2.7 | 29.8 | 0 | 16.7 | 53.5 |
| 4 | 23.5 | 39.7 | 7.0 | 3.8 | 2.6 | 29.9 | 0 | 17.1 | 53.0 |
| 5 | 23.7 | 38.5 | 8.2 | 3.6 | 2.9 | 29.2 | 0 | 17.7 | 53.1 |
| 6 | 24.0 | 38.1 | 8.2 | 3.6 | 2.5 | 30.2 | 0 | 17.5 | 52.3 |
| 19 | 23.3 | 22.0 | 8.0 | 1.6 | 0.9 | 51.3 | 0 | 16.6 | 32.5 |
| 22 | 22.9 | 24.0 | 7.6 | 1.5 | 0.9 | 50.0 | 0 | 16.0 | 34.0 |
| 25.8 | 22.2 | 21.8 | 7.9 | 1.6 | 0.9 | 51.3 | 0 | 16.6 | 32.2 |

Methane conversion and selectivity to $C_2+$ hydrocarbons for the runs ae plotted as a function of time for each run in the attached drawing.

From the results obtained, it can be seen that substantial improvement in the oxidative conversion of methane to higher hydrocarbons was achieved through practice of the invention. Specifically, high catalyst selectivity was maintained over extended reaction times whereas in the comprative run reaction selectivity declined sharply even after only a relatively short time of reaction.

We claim:

1. In a process for oxidative conversion of methane to higher hydrocarbons wherein a mixture of methane and gaseous oxidant is contacted at reaction conditions with a solid oxidative contact agent which is essentially free of reducible metal oxide, the improvement which comprises carrying out said contact of the presence of a chalcogen promoter.

2. The process of claim 1 wherein said oxidative contact agent comprises an alkali metal component.

3. The process of claim 1 wherein said oxidative contact agent comprises an alkaline earth metal oxide.

4. The process of claim 3 wherein said oxidative contact agent comprises an alkali metal component.

5. The process of claim 1 wherein said oxidative contact agent comprises Li promoted MgO.

6. The process of claim 1 wherein said chalcogen is sulfur or a compound of sulfur.

7. The process of claim 1 wherein said chalcogen promoter is $H_2S$.

8. The process of claim 1 wherein the chalcogen promoter is employed in amount of 2 to 1000 ppm. by volume of said gaseous feedstock.

* * * * *